United States Patent [19]

Bandurco et al.

[11] Patent Number: 4,668,787
[45] Date of Patent: May 26, 1987

[54] 5,6-DIALKOXY-4-IMINO-2(1H)QUINAZOLINONE DERIVATIVES

[75] Inventors: Victor T. Bandurco, Bridgewater, N.J.; Stanley C. Bell, Narberth, Pa.; Robert Falotico, Belle Mead; Charles F. Schwender, Califon, both of N.J.; Alfonso J. Tobia, Doylestown, Pa.

[73] Assignee: Ortho Pharmaceutical Corporation, Raritan, N.J.

[21] Appl. No.: 811,238

[22] Filed: Dec. 20, 1985

[51] Int. Cl.$^4$ ........................................... C07D 239/80
[52] U.S. Cl. ................................... 544/286; 544/250; 549/439; 558/417; 558/418

[58] Field of Search ................................. 544/286, 250

[56] References Cited

U.S. PATENT DOCUMENTS 3,464,989 9/1969 Hunter ............................... 544/286
4,146,717 3/1979 Yamamoto et al. ................ 544/286

Primary Examiner—Glennon H. Hollrah
Assistant Examiner—James H. Turnipseed
Attorney, Agent, or Firm—Benjamin F. Lambert

[57] ABSTRACT

Quinazolinone derivatives having an oxy substituent in the 5- and 6-positions are disclosed. The quinazolinone derivatives are useful as cardiovascular agents.

4 Claims, No Drawings

5,6-DIALKOXY-4-IMINO-2(1H)QUINAZOLINONE DERIVATIVES

The present invention relates to novel quinazolinone derivatives having an oxy substituent in the 5 and 6 positions. The novel compounds of the present invention have the following structural formulas:

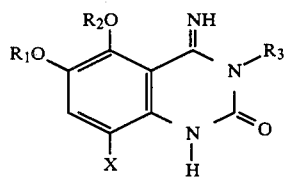

wherein $R_1$ and $R_2$ may be the same or different and are selected from hydrogen, loweralkyl wherein the alkyl group contains 1–6 carbon atoms; or when taken together $R_1$ and $R_2$ form a ring such as a methylenedioxy ring; X is hydrogen or halo, i.e., chloro, bromo, fluoro or iodo; and $R_3$ is loweralkyl wherein the alkyl group is straight or branched chained and contains 1–6 carbon atoms; cycloalkyl having 3–6 carbon atoms; phenyl or substituted phenyl wherein the substituent is loweralkoxy wherein the alkoxy group contains 1–4 carbon atoms, loweralkyl wherein the alkyl group contains 1–6 carbon atoms, halo, i.e., fluoro, chloro, bromo or iodo; nitro; and aralkyl such as benzyl.

Quinazolinones as a class have been reported in the literature and have been described as possessing antihypertensive activity. In particular, 5,6-dimethoxy-2-amino-4-(3H)-quinazolinone is described in J. Med. Chem. 25, 703 (1982).

The compounds of the present invention are prepared according to the following scheme:

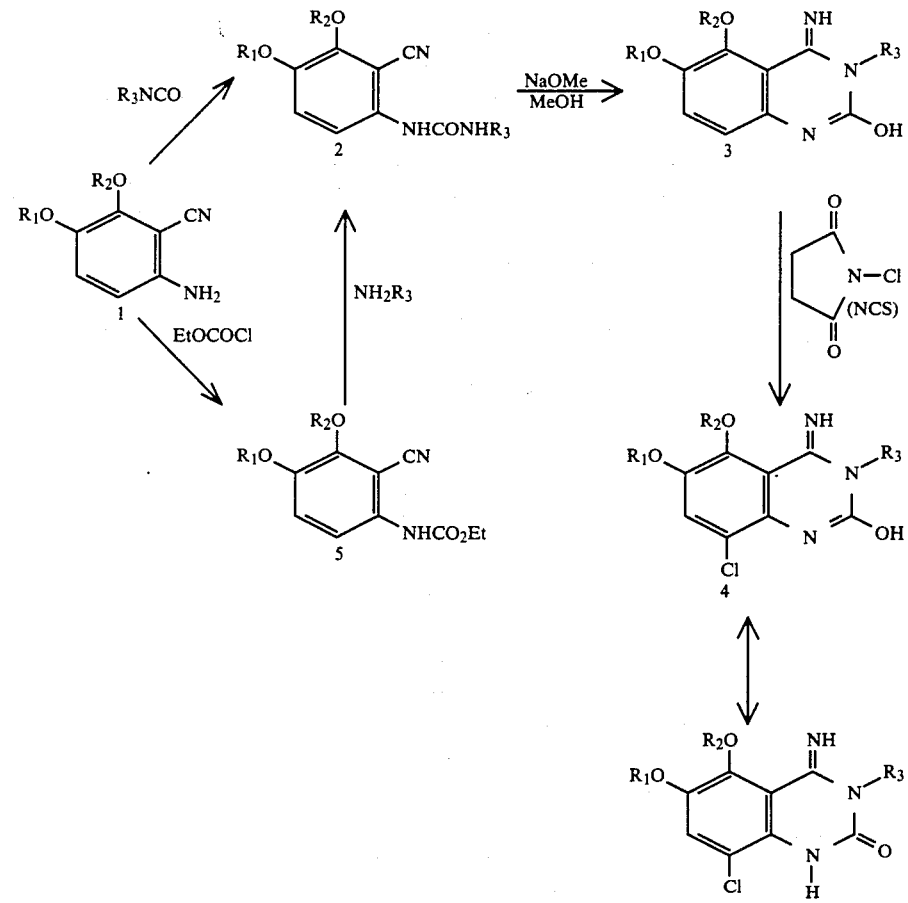

As can be seen from the reaction scheme an anthranilonitrile (1) is first reacted with an appropriately substituted isocyanate to form a substituted urea (2). The reaction is carried out in a suitable solvent such as benzene, dioxane or toluene, for example, at a temperature between about 80° and 110° C. The urea is isolated by techniques known to those skilled in the art. The urea is then cyclized with a base such as sodium methoxide or potassium methoxide, for example, to form the 4-iminoquinazoline (3). The cyclization is carried out in a suitable solvent such as methanol or ethanol at a temperature between about 65° and 80° C. As the cyclizing agent, sodium methoxide or potassium methoxide can be employed. Alternatively, an N-carboethoxyanthranilonitrile (5) is reacted with an amine or an ammonia-ammonium acetate mixture to form the urea (2) which is then cyclized to form a 4-iminoquinazoline (3). The compound (3) may exist either in its enol or keto form. The preparation of the anthranilonitrile intermediate is carried out in a suitable solvent such as chloroform, dioxane or methylene chloride at a temperature between about 50° and 100° C. Those compounds wherein X is halogen (4) are prepared by reacting the quinazolinone (3) with a halogenating agent such as N-chlorosuccinimide or N-bromosuccinimide in a suitable solvent such as chloroform or methylene chloride.

The substituted urea intermediates used in the preparation of the 5,6-dialkoxy quinazolinones are also novel compounds and are part of the present invention.

Also included among the compounds of this invention are the pharmaceutically acceptable acid addition salts prepared from organic and inorganic acids such as, for example, phosphoric acid, hydrochloric acid, hydrobromic acid, hypophosphoric acid, methylsulfonic acid, p-toluenesulfonic acid and sulfuric acid.

The novel quinazolinone derivatives of this invention are active cardiotonic agents.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 0.01 to about 100 mg/kg of body weight and preferably from about 0.1 to about 20 mg/kg of the active ingredient.

The following examples describe the invention in greater particularity and are intended to be a way of illustrating but not limiting the invention.

EXAMPLE 1

2-Amino-5,6-dimethoxybenzonitrile

Iron powder (8.70 g, 156 mmol) was added to a suspension of 2-nitro-5,6-dimethoxybenzonitrile (9.30 g, 44.5 mmol) in an acetic acid (30 ml) and 2-propanol (30 ml) mixture. The mildly exothermic reaction which resulted was allowed to reach 100° and a gentle reflux was maintained for 1 hour with application of heat. Charcoal (10 g) was added, the reaction mixture filtered, and the solid residue obtained was washed with hot 2-propanol (100 ml). The combined filtrates were evaporated to an oily residue which was redissolved in CHCl$_3$ and washed with 5% aqueous NaHCO$_3$ and saturated aqueous NaCl solution. The CHCl$_3$ phase was dried with Na$_2$SO$_4$ and evaporated in vacuo to yield 7.0 g (88.4%) of the target compound as an oil.

EXAMPLE 2

Methyl 2-cyano-3,4-dimethoxyphenylcarbamate

Methyl chloroformate (18.6 g, 19.7 mmol) was added to a suspension of K$_2$CO$_3$ (2.71 g, 19.6 mmol) and 2-amino-5,6-dimethoxybenzonitrile (7.0 g, 39.3 mmol) in 70 ml of CHCl$_3$. The resulting mixture was heated at reflux for 2 hours before being filtered and evaporated to a residual solid. Recrystallization of the crude material from MeOH yielded 4.64 g (50.2%) of product in good purity.

EXAMPLE 3

1-(2-Cyano-3,4-dimethoxyphenyl)3-methylurea

To 2-amino-5,6-dimethoxybenzonitrile (3.4 g, 19.0 mmol) dissolved in 50 ml of benzene, was added 30 mmol of methylisocyanate in benzene. The resultant mixture was refluxed for 0.75 hours and the tan precipitate which formed was collected by filtration. Recrystallization of the crude product from 2-propanol gave 1.59 g (34%) of the analytical urea, mp 236°–237.5°.

EXAMPLE 4

3-Butyl-5,6-dimethoxy-4-imino-2(1H)quinazolinone

A mixture of 1-(2-cyano-3,4-dimethoxyphenyl)-3-butyl urea (5.2 g, 18.8 mmol) in 50 ml of 0.5N methanolic sodium methoxide was heated at reflux under nitrogen for 18 hours. The reaction solution was cooled and a precipitate which formed was collected, washed with cold methanol and dried giving 3.61 g (68.4%) of analytical product, mp 165°–168°.

EXAMPLE 5

3-Butyl-8-chloro-5,6-dimethoxy-4-imino-2(1H)quinazolinone

A solution of 0.5 g (1.77 mmol) of 3-butyl-5,6-dimethoxy-4-imino-2(1H)quinazolinone and N-chlorosuccinimide (0.45 g, 3.35 mmol) in 100 ml of CHCl$_3$ was heated at reflux for 18 hours. The reaction mixture was cooled, washed with 10% aqueous sodium thiosulfate (3×35 ml), dried with anhydrous MgSO$_4$ and evaporated to give the crude product as an orange-brown solid. Recrystallization from 2-propanol afforded the desired product in analytical purity; yield 0.30 g (54.5%) mp 155°–157°.

The following compounds were prepared according to the methods described in Examples 1–6:

TABLE 1

| Ex. | X | R$_3$ | mp. °C. |
|---|---|---|---|
| 7 | H | CH$_3$ | 234–236 |
| 8 | H | C$_2$H$_5$ | 222–224 |
| 9 | H | C$_6$H$_5$ | 262–264 |
| 10 | H | C$_4$H$_9$n | 167–170 |
| 11 | Cl | C$_4$H$_9$n | 155–157 |
| 12 | H | C$_6$H$_4$—4-Cl | 223–225 |
| 13 | H | C$_6$H$_4$—4-NO$_2$ | >300 |
| 14 | H | C$_6$H$_4$—4-OCH$_3$ | 210–212 |
| 15 | H | C$_6$H$_3$—3.4-(OCH$_3$)$_2$ | 218–220 |
| 16 | H | C$_6$H$_4$—3-OCH$_3$ | 256–258 |
| 17 | Cl | C$_2$H$_5$ | 151–153 |

The cardiotonic activity of the substituted quinazolines is determined according to the following general procedure:

Adult mongrel dogs are anesthetized with sodium pentobarbital (45 mg/kg, i.p.) and artificially respired. Arterial pressure (MAP) is recorded via a femoral artery and the pressure pulse is used to trigger a cardiotachometer for heart rate (HR). Left ventricular pressure is measured with a Millar catheter and $dP/dt_{max}$ is derived. A right thoracotomy is performed and cardiac output (CO) is determined by measuring ascending aortic blood flow with an electromagnetic flow probe. Myocardial contractile force (CF) is measured with a Walton Brodie strain gauge sutured to the right ventricle. A lead II EKG is also recorded. A standard dose of dopamine is administered to determine myocardial responsiveness. The biological activity for some of the compounds of the present invention is set forth in Table 2. Compounds are administered by I.V. infusion and dose-related effects of the test compound on MAP, HR, $dP/dt_{max}$, CF and CO are expressed as a percent change from pretreatment control.

The cardiotonic activity of some representative compounds of this invention is tabulated below:

TABLE 2

| X | $R_3$ | Cardiotonic Activity % inc. CF @ 1.87 mg/kg (iv) |
| --- | --- | --- |
| H | $CH_3$ | 69 |
| H | $C_2H_5$ | 132 |
| Cl | $C_4H_9n$ | 42 |
| H | $C_6H_4$—4-$NO_2$ | 6 |
| Cl | $C_2H_5$ | 62 |

CF = Contractile Force

What is claimed:
1. A compound of the formula

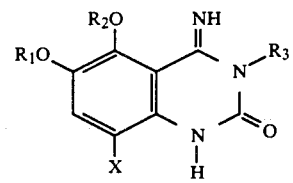

wherein $R_1$ and $R_2$ are hydrogen, alkyl having 1–6 carbon atoms, or when taken together are methylene; X is hydrogen or halogen; and $R_3$ is alkyl having 1–6 carbon atoms, cycloalkyl having 3–6 carbon atoms, benzyl, phenyl or substituted phenyl wherein the substituent is selected from alkoxy having 1–4 carbon atoms, alkyl having 1–6 carbon atoms, halo and nitro and the pharmaceutically acceptable salts thereof.

2. A compound of claim 1 wherein $R_1$ and $R_2$ are alkyl, X is chloro and $R_3$ is alkyl.

3. A compound of claim 1 selected from the group consisting of 5,6-dimethoxy-4-imino-3-methyl-2(1H)quinazolinone; 8-chloro-5,6-dimethoxy-3-ethyl-4-imino-2(1H)quinazolinone; 8-chloro-5,6-dimethoxy-3-methyl-4-imino-2(1H)quinazolinone; 3-butyl-8-chloro-5,6-dimethoxy-4-imino-2(1H)quinazolinone and their pharmaceutically acceptable acid addition salts.

4. A compound of the formula

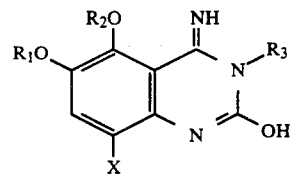

wherein $R_1$ and $R_2$ are hydrogen, alkyl having 1–6 carbon atoms, or when taken together are methylene; X is hydrogen or halogen; and $R_3$ is alkyl having 1–6 carbon atoms, cycloalkyl having 3–6 carbon atoms, benzyl, phenyl or substituted phenyl wherein the substituent is selected from alkoxy having 1–4 carbon atoms, alkyl having 1–6 carbon atoms, halo and nitro and the pharmaceutically acceptable salts thereof.

* * * * *